United States Patent [19]

Camiener

[11] Patent Number: 5,622,696
[45] Date of Patent: Apr. 22, 1997

[54] SAFE DIALDEHYDES USEFUL AS EMBALMING AGENTS

[76] Inventor: Gerald W. Camiener, 26700 Hurlingham Rd., Beachwood, Ohio 44122

[21] Appl. No.: 503,483

[22] Filed: Jul. 18, 1995

Related U.S. Application Data

[62] Division of Ser. No. 149,820, Nov. 10, 1993, Pat. No. 5,429,797.

[51] Int. Cl.$^6$ ........................................ A01N 1/00
[52] U.S. Cl. .................. 424/75; 422/1; 422/36; 422/40; 27/22.1; 27/22.2
[58] Field of Search .................... 424/75; 422/1, 422/36, 40; 27/22.1, 22.2

[56] References Cited

U.S. PATENT DOCUMENTS 3,917,850  11/1975  Boucher .................................. 424/333
4,675,327  6/1987  Fredrick .................................. 514/383

Primary Examiner—Thurman K. Page
Assistant Examiner—James M. Spear
Attorney, Agent, or Firm—Foley & Lardner

[57] ABSTRACT

A group of dialdehydes is disclosed having an even number of atoms in the shortest backbone chain connecting the two aldehyde groups which are useful as decontaminants, fixatives, preservatives, and embalming agents. Compared to conventional aldehydes having an odd number of backbone atoms, the even-numbered dialdehydes are approximately as effective in terms of decontaminant, fixative, preservative and embalming properties, yet they are substantially safer to people, animals, and plants, and the environment.

7 Claims, No Drawings

SAFE DIALDEHYDES USEFUL AS EMBALMING AGENTS

This application is a divisional of application Ser. No. 08/149,820, filed Nov. 10, 1993, now U.S. Pat. No. 5,429,797.

FIELD OF THE INVENTION

The present invention is directed to a specific group of dialdehydes which are useful as decontaminants, tissue fixatives, preservatives and embalming agents, and yet, which are relatively safe compared to conventional dialdehydes and formaldehyde.

BACKGROUND OF THE INVENTION

For more than 100 years, there has been an ongoing search for chemicals that are effective decontaminants, preservatives and fixatives, but which are not seriously dangerous to people and the environment. In particular, compounds are desired that are effective fixatives for biological materials, effective preservatives in embalming procedures, effective agents for viral and microbial decontamination, and effective stabilizers for biological materials like cells, tissues, organs, organisms and bodies.

Also, chemicals have been sought which are effective for decontaminating non-biological materials and objects such as equipment, supplies, instruments, tools, probes, work surfaces, packing supplies, walls, floors, and the like in medical, surgical, food processing, pharmaceutical processing, and other areas where viral and microbial decontamination is important.

One particularly effective group of chemicals that has these desired activities are the aldehydes (see, e.g., U.S. Pat. Nos. 4,343,617 and 4,820,504). Conventionally, aldehydes such as glutaraldehyde and formaldehyde have been used because they interact strongly with biological materials and they cross-link proteins and nucleic acids. Glutaraldehyde is a dialdehyde having an aldehyde group on either end of a propane backbone. It is the two aldehyde groups on either end of the molecule that cause the cross-linking in biological materials and which are responsible for fixation.

Formaldehyde is a monoaldehyde ($CH_2O$) which reacts with biological material just like a dialdehyde by cross-linking. The mechanism of formaldehyde cross-linking is believed to occur in a 2-step reaction wherein formaldehyde first reacts with a reactive hydrogen, such as a non-ionized hydrogen attached to the amino group of a protein, to form a reactive intermediate. The reactive intermediate then reacts with a second reactive hydrogen to form a methylene bridge (cross-link) between the two reaction sites plus water. These reactions are depicted as follows:

(1) $R—H + HCHO \rightarrow [R—CH_2OH]$ (2) $[R—CH_2OH] + R'—H \rightarrow R—CH_2—R' + H_2O$ wherein R and R' are a protein, nucleic acid, or other structure containing a reactive hydrogen. As shown above, formaldehyde can be conceptualized as being a one-carbon dialdehyde.

On the negative side, however, all of the aldehydes that have been used to obtain these desired activities (as noted above) are extremely dangerous to people and to the environment, so much so that their use has been curtailed severely by governmental agencies. Further, these parallel observations of efficacy and dangerousness have led, over the years, to the generally-accepted conclusion that aldehyde reactivity is directly and inseparably linked to the relatively dangerous effects that they have on people, on other forms of life, and on the environment.

However, the present inventor unexpectedly discovered that certain dialdehydes are as active as formaldehyde and glutaraldehyde, yet they are relatively safer to people and the environment. It is this discovery that now will allow certain specific, dialdehydes to be developed and used for the critically needed activities described above. In the absence of this discovery, these dialdehydes would not be developed for commercial use because conventional wisdom has predicted that they, like formaldehyde and glutaraldehyde, would be too dangerous to people. It would have been expected under conventional wisdom that these dialdehydes eventually would be either curtailed, or banned by various governmental agencies. The present invention makes it possible to safely use this important sub-group of dialdehydes as decontaminating agents, tissue fixatives, preservatives, and embalming agents.

DETAILED DESCRIPTION OF THE INVENTION

The present invention is directed to a group of dialdehydes having an even number of atoms in the backbone chain separating the two aldehyde groups (hereafter referred to as "even-numbered dialdehydes") which are useful as decontaminants, preservatives, fixatives, and embalming agents. Unexpectedly, the present inventor discovered that fixative/decontaminant activity can be separated from the dangerous properties of conventional dialdehydes by selecting those dialdehydes with an even number of atoms in the backbone chain. In other words, the fixative/decontaminant activity of a dialdehyde results from the aldehyde groups, while the dangerous properties are a result of the number of atoms separating the two aldehyde groups.

Dialdehydes having an odd number of atoms in the backbone chain separating the aldehyde groups (hereafter referred to as "odd-numbered dialdehydes"), as for example formaldehyde and glutaraldehyde, are very dangerous to people. On the other hand, dialdehydes having an even number of atoms separating the groups are relatively safe to people.

The term "backbone chain" as used herein refers to the series of atoms representing the shortest path, i.e., the path containing the fewest atoms, between the two aldehyde groups (as illustrated in the examples below). The number of atoms in the backbone chain is counted beginning with the first backbone atom bonded to either one of the aldehyde groups and then counting to the next covalently bonded backbone atom in the direction of the shortest path until the last atom is reached which is bonded to the second aldehyde group. If the backbone includes a cyclic moiety, then the shortest path between the aldehyde groups is used to determine whether the backbone chain is odd or even.

For example, butane-1,4-dial, which is an even-numbered dialdehyde according to the present invention would be counted as having two backbone atoms:

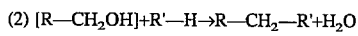

Similarly, 4-hydroxymethyl-2,5-diol-1,6-dial-ethyl-propyl-ether (a reaction product resulting from a periodic acid reaction on β-D-glucopyranose), which contains an ether backbone, would be counted as follows:

Where the backbone chain involves a ring structure, the atoms which form the shortest path (i.e., which contain the least number of atoms) between the two aldehyde groups are counted. For example, benzene-1,2-dial (a ring dialdehyde) would be even-numbered because there are two carbon atoms which most directly connect the two aldehyde groups. Note that in all cases the hydrogen atoms bonded to the backbone atoms are not counted, since they are not part of the backbone chain, nor are the carbon atoms forming the aldehyde groups counted. Similarly, substituents bonded to atoms of the backbone chain are not counted.

Glyoxal (OCH—CHO), which contains no backbone atoms between the two aldehyde groups, is not within the scope of the present invention. This dialdehyde has a unique structure that prevents it from reacting strongly. Because the two aldehyde groups are connected directly to one another, the two aldehyde groups are prevented from being fully reactive. For example, when one of glyoxal's aldehyde groups is acted upon, the reaction affects the other aldehyde group, as well. A well-known example of this phenomenon is the Cannizzaro reaction whereby the oxidation of one aldehyde group to an acid form induces a corresponding internal reduction of the other aldehyde group to a non-reactive alcohol group.

The even-numbered dialdehydes according to the present invention have backbone chains comprising carbon, oxygen, nitrogen and/or sulfur. The backbone chains may be straight, branched, or cyclic. Preferred backbone chains according to the present invention are those containing 2, 4, 6, or 8 atoms. Within this group, preferred backbone chains are those consisting of 2, 4, 6, or 8 carbon atoms. Another group of preferred backbone chains are those containing 2, 4, 6, or 8 atoms, at least one of which is a heteroatom selected from the group consisting of nitrogen, oxygen, and sulfur, and the rest of which are carbon.

Especially preferred even-numbered dialdehydes according to the present invention are those having only carbon in the backbone chain, such as butane-1,4-dial, butane-2,3-diol-1,4-dial, hexane-1,6-dial, octane-1,8-dial, benzene-1,2-dial, and benzene-1,4-dial.

Another preferred group of even-numbered dialdehydes are those containing an ether linkage (an oxygen atom) in the backbone chain. These dialdehydes are formed by periodic acid action on sugar pyranose and furanose compounds.

The even-numbered dialdehydes of the present invention may be used in the form of addition products formed by the reaction of an even-numbered dialdehyde and a reactant selected from the group consisting of bisulfite, water, alcohol, and glycol.

As explained above, the even-numbered dialdehydes of the present invention react in the same way as conventional aldehydes such as formaldehyde and glutaraldehyde, making them useful in a variety of ways. For example, cells and tissues are stabilized when their cell walls, mitochondria, nuclei, and intra-cellular membranes are strengthened and "locked" into place through cross-linking; autolytic decomposition (rotting) is prevented when the autolytic enzymes are inactivated; and microbial decomposition and contagion is prevented through the killing, or inactivation of viruses, bacteria, fungi, and other microbial contagions.

The even-numbered dialdehydes of the present invention may be used in embalming solutions, stabilizing procedures for cells and tissues, histological and cytological reagents, preservation solutions for biological materials, and viral and microbial decontaminating solutions against viruses, fungi, bacteria, and other microorganisms, for use with both biological materials and non-biological materials. Non-biological materials which may be decontaminated according to the present invention include equipment, supplies, instruments, tools, probes, work surfaces, packing supplies, walls, floors, and the like in medical, surgical, food processing, pharmaceutical processing, and other areas where viral and microbial decontamination is important.

Each of these major areas of application will be discussed separately below as they each have their own specific considerations with respect to the even-numbered dialdehydes of the present invention.

Histologic and cytologic fixation procedures require that groups of cells (tissues), the cells themselves, and a wide variety of sub-cellular structures be "locked" spatially in their normal, pre-fixation condition. In order to achieve this effect, the structural components of the cells (comprised primarily of proteins) need to be strengthened and cross-linked to prevent movement, distortion and separation that would otherwise occur during later processing. Also, the tissues and cells need to be protected against decomposition resulting from autolytic enzyme activity and/or microbial decomposition processes.

The even-numbered dialdehydes of the present invention achieve these effects through the normal aldehyde chemical reactions discussed above. Conventionally, the two main aldehydes used in tissue fixation reactions have been formaldehyde and glutaraldehyde, but these aldehydes are so dangerous in a laboratory setting that they are on the verge of being banned. The availability of relatively safe dialdehydes, as provided for by the present invention, will now allow this important medical field to continue to obtain high quality results, while providing safety to both the user and the lab environment.

The relatively safe, even-numbered dialdehydes have been found to be excellent replacements for dangerous formaldehyde and glutaraldehyde. The microscopic quality of tissues and cells prepared with these relatively safe dialdehyde fixatives are equally as good as the dangerous aldehydes, and these even-numbered dialdehydes are compatible with all of the other chemicals that generally are used in fixative solutions.

Biological materials which may be preserved with the even-numbered dialdehydes of the present invention include biological materials from human, non-human animal, and plant sources. In particular, such materials include cells, tissues, organs, organisms, whole bodies, parasites, parasite eggs, blood, urine, and fecal samples.

When preparing solutions comprising the even-numbered dialdehydes of the present invention, other ingredients may be added including osmotic controlling chemicals, alcohols, buffering agents, and divalent, trivalent or transition metal salts. Also, when preparing embalming solutions, conventional ingredients may be employed such as chemicals that provide humectant properties, suppleness of the tissue, coloration, bleaching, and outlining of vascular structures.

Osmotic controlling chemicals include potassium chloride, potassium bromide, lithium bromide, lithium chloride, calcium chloride, calcium phosphate, magnesium chloride, magnesium sulfate, sodium phosphate, potassium phosphate, sodium chloride, sodium bromide, sodium sulfate, sucrose, mannitol, trehalose, polyvinyl alcohol, and polyvinyl pyrrolidone. Such chemicals are used preferably at osmotically-compatible concentrations, either alone or in combination with each other.

Alcohols include mono-, di-, and triols such as methyl alcohol, ethyl alcohol, isopropyl alcohol, ethylene glycol, propylene glycol, glycerol. Preferably, such alcohols are added to the preservative solutions at concentrations ranging from 0.4% to 32% by volume, but some preservative and embalming solutions may include up to 90% by volume.

Buffering agents include citrate buffer, acetate buffer, phosphate buffer, and 2-N-morpholinoethanesulfonate buffer at pH values ranging from pH 3.0 to pH 7.8.

Bivalent and trivalent metal and transition metal salts include salt forms of zinc, aluminum, calcium, magnesium and iron.

Other ingredients include antimicrobial agents, germacides, virucides, decalcifying agents (such as formic, hydrochloric, citric, and nitric acids, and/or their alkali metal or ammonium salt forms), or chelating agents (such as EDTA and its alkali metal or ammonium salts), all of which are used in a conventional manner in fixative solutions.

The present invention is further illustrated by, though in no way limited to, the following examples:

A. COMPARATIVE DIALDEHYDE TESTS

Comparative Example 1

The safety information shown in the following table was taken from reported information found in "Registry of Toxic Effects of Chemical Substances" (RTECS), published jointly by the U.S. Dept. of Health & Human Services, The Center for Disease Control (CDC), and the National Institute of Occupational Safety & Health (NIOSH). Additional safety information can be found in the following listings:

1. National Toxicological Program (NTP);
2. International Agency for Research on Cancer (IARC);
3. Occupational Safety & Health Administration (OSHA); and
4. EPA Gene Tox. Program (EPA-GTP).

SAFETY COMPARISON

| compound | skin irritation | carcinogenicity | reproductive abnormalities |
| --- | --- | --- | --- |
| formaldehyde | 3+ | 3+ | 3+ |
| malondialdehyde | 2+ | 2–3+ | N/L |
| glutaraldehyde | + | 2–3+ | 2+ |
| ethane-1,2-dial | – | – | – |
| butane-1,4-dial | + | – | – |
| butane-2,3-diol-1,4-dial | ± | – | – |
| hexane-1,6-dial | ± | – | – |
| octane-1,8-dial | ± | – | – |
| benzene-1,2-dial | + | – | – |
| benzene-1,4-dial | ± | – | – | key:
"+" indicates dangerous effects in category; the larger the number, the greater the danger
"±" indicates borderline effects in the listed category
"–" indicates no reported effects in the listed category
"N/L" indicates that the chemical is not listed under that category The results clearly show that the odd-numbered dialdehydes (formaldehyde, malondialdehyde, and glutaraldehyde) pose serious health hazards, while the even-numbered dialdehydes, according to the present invention, are substantially safer.

Comparative Example 2

Preservative solutions were prepared in accordance with Working Example 1 (below) except that the aldehydes listed in this table were substituted for the dialdehyde of Working Example 1. Final concentrations of aldehyde were 4% (w/v) in all cases. Rat tissues were treated with the various aldehyde solutions as indicated in Working Example 1. Tissue firmness was determined after 24 hours of fixation, and slides were prepared according to standard histological procedures using conventional hematoxylin and eosin (H & E) staining. Microscopic tissue appearance (microscopic detail) was judged against formaldehyde as the standard. The results are shown in the following table.

PRESERVATIVE EFFECTS

| component | tissue firmness | cellular detail |
| --- | --- | --- |
| formaldehyde | + | + |
| glutaraldehyde | 1–2+ | + |
| butane-1,4-dial | 1–2+ | + |
| benzene-1,4-dial | 1+ | + |
| benzene-1,2-dial | 1+ | + |
| dialdehyde-ether mixture* | 1–2+ | + |

*The dialdehyde-ether mixture is a mixture of dialdehydes prepared by the action of periodic acid on glucopyranose. The actual compounds are 3-hydroxymethyl-4,5-diol-1,6-dial-methyl-butyl-ether, 4-hydroxymethyl-2,5-diol-1,6-dial-ethyl-propyl-ether, and 2-hydroxy-methyl-4,5-diol-1,6-dial-ethyl-propyl-ether. Note that all three species are even-numbered dialdehydes according to the present invention.
key:
"+" firmness indicates the average level of tissue firmness using formaldehyde as the standard
"+" cellular detail indicates a microscopic appearance and quality that is equivalent to that obtained with formaldehyde The results shown in the above table clearly indicate that preservative effects are approximately the same between the even-numbered dialdehydes of the present invention and the conventional odd-numbered dialdehydes.

Comparative Example 3

Embalming solutions were prepared as in Working Example 11 (below) except that the indicated aldehydes were substituted for the dialdehyde of Working Example 11. Final concentrations of the aldehydes were 4% (w/v) in all cases. About 200 ml portions were perfused through dead, 200–300 g, white rats and the rats were left at room temperature for 5 days while covered with towels presoaked in the embalming solutions. Control rats were perfused with methanol-water solutions. "Rotting" was judged by smell (or the lack thereof); "tissue firmness" was judged by feel; and tissue coloration was evaluated at a shaved site. The results are shown in the following table.

EMBALMING EFFECTS

| component | prevention of rotting | tissue firmness | tissue coloration |
| --- | --- | --- | --- |
| formaldehyde | + | + | – |
| glutaraldehyde | + | 1–2+ | – |
| butane-1,4-dial | + | 1–2+ | – |
| benzene-1,2-dial | + | + | + | key:
"+" indicates good prevention of gross tissue decomposition (rotting); average tissue firmness; and some tissue coloration (darkening)
"–" indicates no tissue coloration The results shown in the above table clearly indicate that the even-numbered dialdehydes, according to the present invention, are approximately equivalent to conventional odd-numbered aldehydes in terms of their embalming effects.

Comparative Example 4

The experiments described below in Working Examples 13, 14, and 15 were repeated except that all of the indicated aldehydes were tested in each test system. The results are shown in the following table.

MICROORGANISM-KILLING EFFECTS

| compound | viable bacteria | viable fungi | viable virii |
| --- | --- | --- | --- |
| formaldehyde | 0 | 0 | 0 |
| glutaraldehyde | 0 | 0 | 0 |
| butane-1,4-dial | 0 | 0 | 0 |
| benzene-1,2-dial | 0 | 0 | 0 |
| control (no aldehyde) | $>10^6$ | $>10^6$ | $>10^6$ |

Key:
"0" indicates that no viable bacterium, fungus, or virus was detected (within the error of the assay)
">$10^6$" indicates that the number of bacteria, fungi, and virii detected after the test incubation The results shown in the above table clearly indicate that the even-numbered dialdehydes, according to the present invention, are approximately equivalent to conventional odd-numbered aldehydes in terms of their microorganism-killing effects.

B. WORKING EXAMPLES OF EVEN-NUMBERED DIALDEHYDES

Working Example 1

A preservative solution was prepared in the order shown:

| Component | Amount |
| --- | --- |
| Water | 900 ml |
| $NaH_2PO_4.H_2O$ | 4.0 g |
| $Na_2HPO_4$ | 6.5 g |
| Butane-1,4-dial (40% w/v solution) | 100 ml |

The pH of the solution was approximately neutral. Small pieces of rat tissue were immersed in the solution for several hours, and then processed for histological examination. Good cellular detail was observed with no evidence of autolysis or other degenerative changes.

Working Example 2

A preservative solution was prepared as in Working Example 1 except that 100 ml of water were replaced with 200 ml of denatured ethyl alcohol, and 20 g of benzene-1, 2-dial was substituted for the butane-1,4-dial. Another preservative solution was prepared in the same manner except that the 100 ml of water was not replaced with 200 ml of denatured alcohol.

Rabbit kidneys were cut in half and one half of each kidney was tested in each solution. The kidney halves were immersed in at least 10-times their volume of the prepared solutions and allowed to stand for different periods of time. The halves were then processed for pathological and histological examination.

After 6 hours of exposure to the solutions, the center-most portions of the kidney showed good penetration of the solution containing the alcohol while the other kidney halves, which were treated with the solution lacking alcohol, showed substantially poorer penetration in the center-most portions.

Working Example 3

Kidneys prepared and treated in accordance with Working Example 2 were examined after 7 and 21 days of immersion in the solution containing alcohol. The kidneys remained in good stabilized condition suitable for pathologic and histologic examination. Good cellular detail was observed with no observable degradative changes.

Working Example 4

To a glass container, there was added, in the following order with mixing, 850 ml of denatured ethyl alcohol, 50 ml of glacial acetic acid and 100 ml of a 40% butane-1,4-dial solution. Various arachnids, insects and plant parts were immersed in the solution and examined after one week and three weeks of immersion. All tissues, cells and organisms showed good preservation and good cellular detail.

Working Example 5

To a glass container, there was added, in the following order with mixing, 950 ml of deionized water, 45 g mercuric chloride, 5 g of sodium chloride, 20 g of trichloroacetic acid, 40 ml of glacial acetic acid, and 20 g of benzene-1,2-dial. Pieces of human lymph node tissue were immersed in the solution from 3 to 24 hours. Subsequent histological processing and examination showed good preservation and good cellular detail with negligible shrinkage of the tissue.

Working Example 6

To a glass container, there was added, in the following order with mixing, 850 ml of deionized water, 10 g of formic acid, 100 g of trisodium citrate, and 100 ml of a 40% butane-1,4-dial solution. Pieces of bovine bone were immersed in at least a 10-fold excess of the solution and left for 5–7 days. Subsequent processing and examination showed good preservation and good cellular detail. Calcified areas were completely decalcified and shrinkage was not observed.

Working Example 7

The formic acid in Working Example 6 was replaced with 100 g of disodium ethylene-diamine-tetraacetate. Subsequent processing and examination showed good preservation and structure. Good decalcification was observed.

Working Example 8

A test-stable stool sample kit was prepared to maintain a stool sample in a condition suitable for analysis at a later time by an appropriate laboratory. The kit included a male receptacle means and a female closure means, and 30 ml of an aqueous solution which contained the solution described in Working Example 1. The male receptacle means was a 2 oz. wide mouth plastic container with a screw pattern to accommodate a female screw cap closure. It is to be understood that the male receptacle means may be of any shape, size or form, provided that it can accommodate a small sample of stool that is to be inserted into the male receptacle means.

Parasites in the stool sample which were the object of laboratory examination were preserved in the stool samples by the fixative solution so as to permit the stool sample to be properly used to identify the presence of such parasites.

Working Example 9

A freshly excised sheep heart was perfused with a solution identical to the first solution prepared in Working Example 2. Following perfusion, the heart was left immersed in a closed container for 3 weeks, and then examined macroscopically and microscopically. The heart was preserved in good condition with no apparent degradative changes, and was suitable for student observation.

Working Example 10

An adult bull frog was extinguished under ether, and then perfused with the first solution described in Working Example 2 to which sodium chloride (0.6%) and cetyltrimethylammonium bromide (0.15%) were added. The frog was kept moistened with the same solution (under wetted cotton) in a closed container. The frog remained suitable for student dissection for a period of at least one month.

Working Example 11

An embalming composition was prepared in the order shown:

| Component | Amount |
| --- | --- |
| Water | 700 ml |
| Butane-1,4-dial (40%) | 100 ml |
| Methanol | 200 ml |
| Water | to 1 liter |

Between 25 and 50 liters of the above solution were perfused into a human body by means of generally accepted embalming techniques. Examination of the body several days later showed excellent preservation, both grossly (as measured by appearance), and by lack of decomposition. On dissection, good internal tissue, organ, and vascular structure were observed.

Working Example 12

An embalming composition was prepared in the order shown:

| Component | Amount |
| --- | --- |
| Water | 700 ml |
| Benzene-1,2-dial | 100 g |
| Methanol | 200 ml |
| Glycerol | 80 ml |
| Borax | 20 g |
| Sodium Nitrate | 40 g |

Approximately 4–5 liters was perfused through a dead adult cat; about 100 ml was perfused through a dead frog (about 50 g in weight); about 300 ml was perfused through a sheep heart; and about 500 ml of the composition was used to immerse several earthworms and grasshoppers. After several days, the different specimens were examined. Preservation was excellent both as seen grossly and as seen on dissection.

Working Example 13

To a 1.0% solution of butane-1,4-dial in deionized water was added a 0.1 ml aliquot of inoculum containing a rapidly-dividing culture of *Pseudomonas aeruginosa* (48 hours old, 37° C.) in tryptic-soy broth at a concentration of about $1 \times 10^7$ viable bacteria per ml. After 30 minutes of incubation at room temperature, aliquots of the suspension were diluted out, and were plated for counting. No bacterial colonies (no viable bacteria) were observed. Complete killing had been achieved (as determined within the error of the assay).

Working Example 14

The experiment described in Working Example 13 was repeated except that benzene-1,2-dial was tested against a fungus, *Chaetonium globosum*, with incubation at 25° C. (instead of 37° C.). No fungal colonies were observed on plating following the decontamination step (i.e., complete killing had been achieved within the error of the assay).

Working Example 15

A decontaminating solution was prepared as in Working Example 1 except that the final concentration of the butane-1,4-dial was 0.5% (w/v). Films of virus (HIV-1) dried on glass surfaces were exposed to the solution according to test criteria and methods defined by the U.S. Environmental Protection Agency (EPA) for registration of a material as a viricide. Following exposure, the test solution was separated from the virus particles by Sephadex gel filtration, and the virus was titrated for HIV-1 lytic cytopathogenic effects (CPE). No CPE was observed in the treated preparations indicating that complete killing (viral inactivation) had occurred.

Working Example 16

The experiment described in Working Example 15 was repeated using a 50% solution of sheep blood (w/v) in place of the water and salts to prepare the solution of butane-1,4-dial. Again, no CPE were observed indicating that complete killing had been achieved.

Working Example 17

Sheep blood was collected in a standard citrate collection medium. The cells were washed 5 times in 8–10 volumes (of the packed cell volumes) with isotonic glucose-saline, and re-suspended in pH 8.5 citrate buffer (5.25% in deionized water) at a 10% concentration (10 ml of packed cell volume in 100 ml of cell suspension). An equal volume of 4% butane-1,4-dial solution (w/v) was added to the cell suspension with continuous mixing at room temperature, and left with gentle agitation for 20–24 hours. The cells were then washed 5 times with glucose-saline, re-suspended in citrate buffer at a 10% concentration, treated a second time with the butane-1,4-dial solution, and washed 5 times with glucose-saline.

Finally, the cells are re-suspended at a 10% concentration in 0.1M phosphate buffer at pH 7.0 containing 0.1% sodium azide as an antimicrobial agent. The cells were then evaluated in both hemagglutination assays and for long-term storage. The results in both evaluations were excellent and were equivalent to controls that were prepared using cells stabilized with formaldehyde at equivalent concentrations.

While the invention has been described in detail and with reference to specific embodiments thereof, it will be apparent to one skilled in the art that various changes and modifications can be made therein without departing from the spirit and scope of the invention.

I claim:

1. A method of embalming a human, non-human animal, or plant body or organ which comprises treating said body or organ with an aqueous solution comprising from about 0.4% to about 40% (weight/volume) of a dialdehyde wherein the shortest backbone chain linking the two aldehydes is a chain of 2, 4, 6, or 8 atoms which are selected from the group consisting of carbon, oxygen, nitrogen, and sulfur.

2. A method according to claim 1 wherein the atoms of the backbone chain are all carbon atoms.

3. A method according to claim 1 wherein the dialdehyde is selected from the group consisting of butane-1,4-dial, butane-2,3-diol-1,4-dial, hexane-1,6-dial, octane-1,8-dial, benzene-1,2-dial, and benzene-1,4-dial.

4. A method according to claim 1 wherein the backbone chain includes at least one heteroatom selected from the group consisting of nitrogen, oxygen, and sulfur.

5. A method according to claim 1 wherein the dialdehyde has a backbone chain containing an ether linkage and said dialdehyde is formed by the reaction of periodic acid on sugar pyranose and furanose compounds.

6. A method according to claim 1 wherein the dialdehyde is a dialdehyde addition product formed by the reaction of the dialdehyde and a reactant selected from the group consisting of bisulfite, water, alcohol, and glycol.

7. A method according to claim 1 wherein the dialdehyde is present in an amount of from 0.4% to 40% (weight/volume) of the overall solution.

* * * * *